United States Patent [19]

White et al.

[11] Patent Number: 5,086,073
[45] Date of Patent: Feb. 4, 1992

[54] COMPOSITION FOR TREATING DEPRESSION WITH ARALKYL AMINES

[75] Inventors: John F. White, Wokingham; Michael C. Warren, Oxford; Christine Ennis, Maidenhead, all of England

[73] Assignee: John Wyeth & Brother Limited, Maidenhead, England

[21] Appl. No.: 530,758

[22] Filed: May 30, 1990

[30] Foreign Application Priority Data

Jun. 2, 1989 [GB] United Kingdom ............ 8912784.9
Nov. 30, 1989 [GB] United Kingdom ............ 8927087.0

[51] Int. Cl.$^5$ ................ A61K 31/13; A61K 31/18; A61K 31/135; A61K 31/445
[52] U.S. Cl. ................................. 514/602; 514/604; 514/647; 514/649; 514/650; 514/655; 514/657; 514/660; 514/315; 514/359
[58] Field of Search ............... 514/655, 649, 602, 604, 514/647, 650, 657, 660, 315, 359

[56] References Cited

FOREIGN PATENT DOCUMENTS 177078 4/1986 European Pat. Off. .
1343543 1/1974 United Kingdom .

OTHER PUBLICATIONS

Chem. Abst. 59: 11543e—abstract of Belgium Pat. No. 619,890, publ. 1/7/63 to Olin Mathieson (abstract only).
Shapiro et al., J. Amer. Chem. Soc., 81, 3728-3736 (1959).
Labriola et al. Anales asoc. quim.—Argentina, 37, 79-96 (1949) (Spanish with Eng. summary).
Chem. Abst. 86: 56227x—abstract of Czech. Pat. No. 163580 (AU') publ. 7/15/76 to Weisner (Patent in Czech).
Hoffmann, et al., J. Med. Chem. 18, 278-284 (1975).
Brimblecombe, et al., Brit. J. Pharmacol., 23, 43-54 (1964).
Buck et al., J. Amer. Chem. Soc., 63, 1964-1966 (1941).
Chem. Abst. 51: 8287d—abstract of Reiff, Acta Trop., 13, 289-318 (1956) (in German)—(Abstract only).

Primary Examiner—Stanley J. Friedman
Attorney, Agent, or Firm—Arthur G. Seifert

[57] ABSTRACT

The invention concerns compounds having formula:

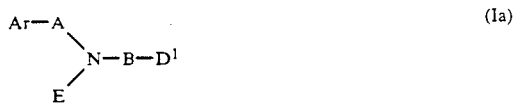

or a salt thereof, wherein E represents hydrogen, lower alkyl or a group $Ar^1-A^1$; Ar and $Ar^1$ are the same or different aryl groups (including heteroaryl) which are optionally substituted, e.g. by one or more substituents commonly used in pharmaceutical chemistry; A and $A^1$ are the same or different alkylene groups having one or two carbon atoms linking Ar or $Ar^1$ to N and optionally substituted by lower alkyl and/or optionally substituted aryl, B is an alkylene group of 3 or 4 carbon atoms, which may be substituted by lower alkyl; $D^1$ represents halogen, $CH_3$, $CR^1R^2NH_2$, $SO_3H$ or $SO_2NR^6R^7$ where $R^1$ and $R^2$ are independently hydrogen or lower alkyl and $R^6$ and $R^7$ are each hydrogen, lower alkyl or aralkyl of 7 to 12 carbon atoms or $R^6$ and $R^7$ together with the nitrogen atom to which they are attached represent a 5 or 6 membered ring, which compounds are useful, for treating depression or cerebral insufficiency or dementias in animals.

30 Claims, No Drawings

COMPOSITION FOR TREATING DEPRESSION WITH ARALKYL AMINES

This invention relates to amines possessing a new pharmacological activity, to processes for preparing them and to pharmaceutical compositions containing them. More particularly this invention relates to amines useful in the treatment of depression.

In the UK the annual referral rate for depression is around 300-400 per 105 population of whom 10-15% require hospitalisation. At present the most effective and safe treatment for severe depression involves electroconvulsive therapy (ECT) where the patient receives a series of controlled electric shocks. However such treatment understandably engenders an atavistic fear and apprehension in many patients. It also has undesirable side-effects, notably disturbance of memory.

ECT is also expensive and time-consuming to administer, requiring the presence of specialist doctors such as psychiatrists and anaesthetists. As an alternative to ECT, drug therapy provides a more acceptable treatment for the patient but at the present time such therapy has not displaced ECT as the optimal treatment in severe cases because it is not always effective. There is therefore a need for new drugs for the treatment of depression, especially drugs having new modes of action mimicking ECT.

The mode of action of ECT remains unknown but in recent years much has been learnt about the biological effects of electroconvulsive shock (ECS) in animals. In particular, repeated ECS, given in ways closely mimicking those used to administer ECT clinically, elicits in rodents changes in monoamine functions.

These include: increased 5-HT-mediated behaviour, increased dopaminergic behaviour and depressed beta-adrenoceptor binding and sensitivity of the coupled adenylate cyclase. The last is also seen following chronic treatment with a number of antidepressant drugs.

The effects of repeated ECS are presumably a response or adaptation to the acute effects of the seizures. Among these acute effects are a marked change in the release, synthesis and level of gamma aminobutyric acid (GABA) in the brain.—see Green A. R. et al, British J. Pharmacol., 92, 5-11 and 13-18 (1987) and Bowdler et al, ibid, 76, 291-298 (1982).

GABA is one of the most widespread and abundant transmitters in the mammalian central nervous system and plays a major role in the control of brain excitability. It is similarly implicated in the benzodiazepine-mediated relief of anxiety. Recently, evidence has come to light which suggests that GABA transmission may also be involved in the therapeutic effects of some antidepressant treatments. In particular, new compounds designed as GABA agonists (e.g. fengabine and progabide) have been shown in preliminary clinical trials to have antidepressant activity (vide infra). Taken together, these findings suggest that interventions directed specifically at GABA transmission may provide the basis of novel therapies for the treatment of affective disorders.

At present three GABA receptors have been identified in the central nervous system. These are (1) a $GABA_A$-receptor known to be mainly postsynaptic and mediating inhibition of neuronal firing—see for example Stephenson, F. A. Biochem. J., 249 pp 21-32 (1988); (2) a $GABA_B$ receptor located presynaptically and mediating the inhibition of release of a number of neuro-transmitters, e.g. noradrenaline and aspartic acid, but not GABA—see for example Bowery, N. G. et al, Nature, 283, 92-94 (1980); and (3) a GABA autoreceptor which modulates the release of GABA from neurones—see for example Mitchell, P. R., and Martin, I. L. Nature, 274 904-905 (1978); Arbilla, S. Kanal, J. L and Langer, S. Z. Eur.J.Pharmac., 57, 211-217 (1979) and Brennan M. J. W. et al, Molec. Pharmac., 19, 27-30 (1981).

The pharmacological importance of these receptors is currently a subject of investigation with a major part of the work involving the search for anticonvulsant drugs with a mode of action involving $GABA_A$ receptors. Two drugs acting on GABA receptors, progabide and fengabine, have also been shown to possess antidepressant effects in preliminary clinical trials—see P. L. Morselli et al, L.E.R.S. Vol 4 (1986) pp 119-126 and B. Scatton et al, Journal of Pharm. and Exp. Therapeutics., 241, 251-257 (1987). The latter workers showed that fengabine possessed a biochemical mode of action different from that of conventional antidepressants but that the mechanism whereby fengabine exerted its antidepressant actions was not yet clear. It was thought to derive from a GABAergic action, most likely at $GABA_A$ receptors.

In the case of progabide, Morselli et al also attributed the antidepressant effect to an increased GABAergic transmission.

In copending UK patent application 8813185.9 filed June 3, 1988 evidence is provided that the antidepressant effect of progabide and fengabine is in fact due to their agonist action at the GABA autoreceptor. The GABA autoreceptor is capable of regulating the release of GABA from GABAergic neurons which means an agonist at the autoreceptor would decrease the GABA release hence decreasing GABA function i.e. an action opposite to that of $GABA_A$ agonists. Previously the autoreceptor was believed to have the same pharmacology as the $GABA_A$ site—see Molec. Pharm, 19,27-30 (1981). We have found that the GABA autoreceptor has its own distinct pharmacology and that there are compounds having selective agonist activity at the GABA autoreceptor. These compounds have valuable medical uses.

There is also evidence that compounds acting at the benzodiazepine receptor as inverse agonists decrease GABA function in the brain and thus increase acetylcholine transmission. In addition, probably as a consequence of these actions, they facilitate memory in animals and man (see Sarter. M. et al. Trends in Neuroscience, 11 13-17, 1988). Compounds acting selectively as GABA autoreceptor agonists are believed to have similar actions such as nootropic activity (e.g. increased vigilance and cognition) and are therefore useful in the treatment of cerebral insufficiency disorders and dementias.

Accordingly this invention provides a compound for use as a pharmaceutical having formula:

(Ia)

or a salt thereof, wherein E represents hydrogen, lower alkyl or a group $Ar^1—A^1—$; Ar and $Ar^1$ are the same or different aryl groups (including heteroaryl) which are optionally substituted, e.g. by one or more substituents commonly used in pharmaceutical chemistry such as lower alkyl, lower alkoxy, halogen, haloloweralkyl, haloloweralkoxy, cyano, amino (including substituted amino e.g. mono- or di-loweralkyl amino) and nitro; A and $A^1$ are the same or different alkylene groups having one or two carbon atoms linking Ar or $Ar^1$ to N and optionally substituted by lower alkyl and/or optionally substituted aryl, B is an alkylene group of 3 or 4 carbon atoms, which may be substituted by lower alkyl; $D^1$ represents halogen, $CH_3SO_3H$, $CR^1R^2NH_2$ or $SO_2NR^6R^7$ and $R^1$ and $R^2$ are independently hydrogen or loweralkyl and $R^6$ and $R^7$ are independently hydrogen, lower alkyl aralkyl of 7 to 12 carbon atoms or $R^6$ and $R^7$ together with the nitrogen to which they are attached form a 5 or 6 membered ring; e.g. pyrrolidine or piperidine. By the term "lower" is meant a group containing 1 to 6 carbon atoms. Examples of lower alkyl are methyl, ethyl, propyl and butyl.

Examples of $D^1$ include halogens such as fluorine, chlorine or bromine, $SO_2NH_2$, $SO_2NMe_2$ and $CH_2NH_2$. Examples of Ar and $Ar^1$ are mono- or bi-cyclic aryl groups such as carbocyclic aryl groups of 6 to 10 carbon atoms (e.g. phenyl or naphthyl) and heteroaryl groups of 5 to 10 ring atoms in which the heteroatom is selected from oxygen, nitrogen and sulphur (e.g. pyridine, furan, thiophene) or aromatic groups containing two or more such heteroatoms (e.g. thiazolyl). Bicyclic heteroaryl groups are exemplified by quinoline and benzofuran.

Examples of A and $A^1$ are independently $—(CH_2)_m—$ optionally substituted by lower alkyl and/or aryl where m is 1 or 2. Preferably A and $A^1$ are independently $CHR^3—$ where $R^3$ is hydrogen, lower alkyl, e.g. methyl or ethyl, or optionally substituted aryl as defined for Ar, e.g. phenyl. Examples of B are $—CH_2CH_2CH_2—$ and such a group substituted by lower alkyl such as methyl, e.g. B represents $—CH(CH_3)CH_2CH_2—$ or $—CH_2CH(CH_3)CH_2—$.

Examples of $R^1$ and/or $R^2$ are hydrogen and methyl.

In a further aspect this invention provides a compound of formula Ia or a salt thereof as defined above. This invention also provides a pharmaceutical composition comprising a compound of formula Ia or a pharmaceutically acceptable salt thereof and a pharmaceutically acceptable carrier.

The compounds of formula Ia as defined above possess pharmacological activity especially activity affecting the nervous system. In particular the compounds of formula Ia are inhibitors of gamma aminobutyric acid (GABA) release from nerve terminals via action on the GABA autoreceptor.

A number of compounds have previously been shown to be agonists at the GABA autoreceptor, for example muscimol, isoguvacine and THIP (see Merck Index 1983 No. 9214) but such compounds are non-selective in that they are also active at other GABA receptors (i.e. $GABA_A$ and/or $GABA_B$). As far as we are aware no medical use has been attributed to the above-mentioned compounds based on their GABA autoreceptor activity.

Compounds showing selective properties at the GABA autoreceptor are desirable since additional activity at the other GABA receptors would cause many side effects such as sedation and adverse muscle tone actions.

The compounds of formula Ia demonstrate activity at GABA autoreceptors, more specifically they demonstrate agonist activity as shown by standard in vitro test procedures. Advantageously compounds of formula Ia appear to be selective in that they display little or no activity at $GABA_A$ or $GABA_B$ receptors. The following test procedures were used to measure activity at (a) GABA autoreceptors and $GABA_B$ receptors by inhibition of potassium-evoked GABA and noradrenalin release from rat cortex in vitro (Procedure 1); and (b) $GABA_A$ receptors by depolarisation of the isolated rat vagus nerve, (Procedure 2)

Procedure (1)

Slices ($0.25 \times 0.25 \times 2.0$ mm) of rat cerebral cortex are prepared using a McIlwain tissue chopper. The slices are incubated in Krebs-Henseleit solution containing [$^3$H]-GABA ($10^{-7}$M) and [$^{14}$C]-noradrenaline ($10^{-7}$M) in the presence of amino-oxyacetic acid (AOAA) ($10^{-5}$M), pargyline ($10^{-6}$M) and ascorbic acid ($10^{-4}$M), for 20 minutes at 37° C., rinsed with 5 ml aliquots of Krebs-Henseleit solution and transferred to 10 superfusion chambers (volume 300 μl). The slices are continuously superfused with Krebs-Henseleit solution (0.4 ml min$^{-1}$) containing AOAA ($10^{-5}$M) and fractions of the superfusate collected every 4 minutes. Transmitter release is induced by 4 minute exposure to a Krebs-Henseleit solution containing 25 mM potassium (with concomitant reduction in sodium to maintain osmolarity) after 68 ($S_1$) and 92 ($S_2$) minutes of superfusion. The compound under study is added to the superfusing medium 20 minutes prior to the second potassium stimulation. The residual radioactivity in the slices at the end of the experiment together with that in the superfusate fractions is measured by liquid scintillation counting using a dual label programme for tritium and carbon-14.

Calculations: The amount of radioactivity (either tritium or carbon-14) in each fraction is expressed as a percentage of the respective total radioactivity in the tissue at the start of the respective collection period. The amount of radioactivity released above basal by the increased potassium is calculated and the ratio S2/S1 obtained. The S2/S1 ratio from drug-treated slices is expressed as a percentage of the control S2/S1 ratio. For compounds achieving inhibition of 30% or more $pD_2$ values are calculated from plots of inhibition of release versus concentration of drug. Failure to inhibit the release of noradrenaline indicates that the molecule has no $GABA_B$ agonist activity.

Procedure (2)

Male Sprague-Dawley rats (250–400 g) are killed by a blow to the head and cervical dislocation. The cervical vagus nerves are transferred into Krebs' solution at room temperature and the connective tissue sheath removed. The vagus nerves are placed in two-compartment Perspex baths to permit extracellular recording of agonist induced depolarizations. Each nerve projects from one compartment to the next by way of a grease filled slot, the grease serving to insulate the compartments from each other. The d.c. potential between the compartments is recorded using silver-silver, chloride electrodes in saline-agar bridges and displayed on a Grass polygraph. One compartment is continuously perfused (5 ml min$^{-1}$) with Krebs' solution at 27° C. to which agonist and antagonist drugs are added. The second compartment remains filled with Krebs' solution alone. Non-cumulative concentration-response curves to GABA ($10^{-6}$ to $3 \times 10^{-4}$M) are obtained using a 5 min contact time and 10–20 min wash period and the effect of the test compound is compared to that of GABA.

RESULTS

In the aforementioned tests the following representative compounds gave the results shown:

| Compound | GABA autoreceptor pD2 values | Inhibition of release of noradrenaline at $10^{-5}$M | Depolarisation of rat vagus nerve at $10^{-4}$M |
|---|---|---|---|
| N-Butyl-N-methyl-4-chlorobenzenemethanamine | 6.3 | no effect | no effect |
| N-Butyl-N-methyl-benzenemethanamine | 7.0 | " | " |
| N,N-Bis-(4-chlorobenzyl)butylamine | 6.8 | no effect | not tested |
| N-Butyldibenzylamine | 6.2 | " | " |
| N,N-Bis(phenylmethyl)-1,4-diaminobutane | 6.0 | " | " |

In another aspect this invention provides use of a compound of formula Ia for the preparation of a medicament for the treatment of senile dementia and/or depression.

This invention also provides processes for preparing the compounds of the invention. Compounds of formula Ia may be prepared by any one of the following processes:

a) alkylating a compound of formula II, IIa or IIb

    II

    IIa

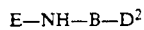    IIb wherein Ar, E and A are as defined above and $D^2$ is $CH_3$ with an appropriate compound of formula III; IIIa or IIIb:

hal—B—CN    (III)

$E^1$—hal    (IIIa)

Ar—A—hal    (IIIb)

wherein B, Ar and A are as defined above, hal represents chlorine or bromine, and $E^1$ is E excepting hydrogen, to give a compound of formula Ia wherein $D^1$ is $CH_3$, or $SO_2NR^6R^7$ or b) carrying out a reductive alkylation of a compound of formula II, IIa or IIb as defined above using an appropriate compound of formula IV, IVa or IVb

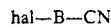    (IV)

    (IVa)

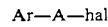    (IVb)

wherein $D^2$ is as defined above, $E^2$ is alkyl of 1 to 5 carbon atoms or $Ar^1$—$CH_2$—, $A^2$ is $CH_2$ and $B^1$ is an alkylene chain of 2 or 3 carbon atoms optionally substituted by lower alkyl, in the presence of a reducing agent such as sodium cyanoborohydride to give a corresponding compound of formula Ia wherein $D^1$ is $CH_3$ or $SO_2NR^6R^7$; or (c) reducing a compound of formula (V)

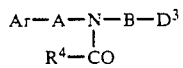    (V)

wherein $D^3$ is $CH_3$, $CR^1R^2NH_2$ or $CONH_2$, $R^4$ is alkyl of 1 to 5 carbon atoms or $Ar^1$—$A^2$—; Ar, $Ar^1$, A and B are as defined above, and $A^2$ represents a direct bond or alkylene of 1 carbon atom optionally substituted by lower alkyl and/or aryl to give a corresponding compound of formula Ia as defined above wherein $D^1$ is $CH_3$ or $CR^1R^2$ $NH_2$ and E is $R^4CH_2$ wherein $R^4$ is as defined above; or (d) reducing a compound of formula (VI)

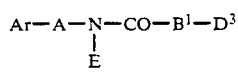    (VI)

wherein Ar, A and E are as defined above $D^3$ is as defined above and $B^1$ is as defined in connection with formula IV to give a corresponding compound of formula I wherein B is —$CH_2B^1$— and $D^1$ is $CH_3$ or $CR^1R^2NH_2$; or (e) reacting a compound of formula

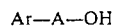    (VII)

with an amine of formula:

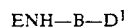    (VIII)

wherein Ar, A, E and B are as defined above and $D^1$ is $CH_3$ in the presence of an acid, e.g. $H_2SO_4$ to give a compound of formula I wherein $D^1$ is $CH_3$, or (f) performing a Mannich reaction with an aryl anion of formula $Ar^\ominus$, formaldehyde and an amine of formula VIII to give a compound of formula Ia wherein $D^1$ is $CH_3$ or (g) halogenating a compound of formula

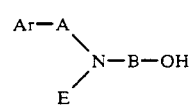    (IX)

wherein Ar, A, B and E are as defined above, e.g. using thionyl chloride, phosphorus oxychloride, $PBr_3$ or an acid HX where X is halogen, to give a compound of formula Ia wherein $D^1$ is halogen or (h) reacting a compound formula X

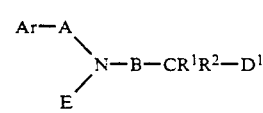    (X)

wherein $D^1$ is halogen e.g. chlorine with (i) an alkali metal azide followed by hydrogenation, e.g. $H_2/Pd$, or (ii) performing a Gabriel synthesis, to give a corresponding compound of formula Ia wherein $D^1$ is $NH_2$ or (i) reducing a compound of formula

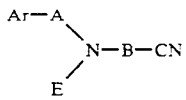 (XI)

wherein Ar, A, E and B are as defined above, e.g. using lithium aluminium hydride to give a compound of formula Ia wherein $D^1$ is —$CH_2NH_2$; or (j) oxidising a compound of formula

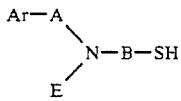 (XII)

therein Ar, A, B and E are as defined above to give a corresponding compound of formula I wherein $D^1$ is $SO_3H$, or (k) reacting a reactive derivative of a compound of formula

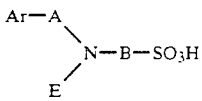 (XIII)

wherein Ar, A, E and B are as defined above with an amine of formula $HNR^6R^7$ (XIV)

to give a corresponding compound of formula I wherein $D^1$ is $SO_2NR^6R^7$ or (1) acidifying a compound of formula Ia to give an acid addition salt thereof or neutralising an acid addition salt to give the free base form; or (m) reacting a of formula II with a sultone of formula

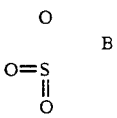

to give a compound of formula I wherein $D^1$ is $SO_3H$ or a salt thereof. With regard to process (a) the reaction may be conveniently carried out in the presence of an inert solvent and a base such as a tertiary amine (e.g. diisopropylethylamine) with heating if required. Examples of suitable inert solvents are dimethylformamide, acetonitrile and dimethylsulphoxide. With regard to process (b) the reductive alkylation is conveniently carried out in an inert solvent, depending on the reducing agent, and without heating. When the reducing agent is sodium cyanoborohydride the solvent may be an aqueous alcohol such as aqueous ethanol. Catalytic hydrogenation may also be used, e.g. using Pd/C and an alcohol solvent, e.g. ethanol. Process (c) and (d) may both be carried out using a suitable reducing agent for example ionic hydrogenation see Kursanor et al, Synthesis 1974, Vol 9, 633-651. Other reducing agents may be used, e.g. diborane, Raney nickel or $LiAlH_4$. Process (k) may be carried out in an inert solvent by forming a reactive derivative of the acid of formula XIII in situ (such as the sulphonyl halide prepared by adding $PCl_5$). In order to avoid internal quaterisation the initial reactive intermediate is not purified but is at once treated with the amine of formula XIV. Process (m) may be carried out in an inert solvent e.g. an alkanol without heating. The starting materials of formula II used in process (a) are known compounds or can be prepared by analogous methods e.g. by reducing an amide of formula Ar—A—NHCO—$E^1$ where $E^1$ has one $CH_2$ group less than E.

Compounds of formula V can be prepared by acylating a corresponding compound of formula Ar—A—N-H—B—$D^1$ using an acid chloride of formula $R^4$COCl. Compounds of formula Ar—A—NH—B—$D^1$ can themselves be prepared by alkylating amines of formula $NH_2$—B—$D^1$ using a halide of formula Ar—A—hal.

Compounds of formula VI can be prepared by acylating amines of formula Ar—A—NH—E using an acid chloride of formula $ClCO.B^1$—$D^1$ wherein $B^1$ has the value defined in connection with process (d).

Compounds of formula XII may be prepared by hydrolysing the corresponding isothiouronium salt in the presence of base, e.g. NaOH. The isothiouronium salt may be prepared from a compound of formula I wherein $D^1$ is halogen using thiourea.

Starting materials for the processes described herein are known compounds or can be prepared by analogous methods for known compounds.

In any of the aforementioned reactions compounds of formula (and Ia) may be isolated in free base form or as acid addition salts as desired. Examples of such salts include salts with pharmaceutically acceptable acids such as hydrochloric, hydrobromic, hyroiodic, sulphuric, phosphoric, nitric, acetic, citric, tartaric, fumaric, succinic, malonic, formic, maleic acid or organosulphonic acids such as methane sulphonic or tosylic acid.

When acidic substituents are present it is also possible to form salts with strong bases e.g. alkali metals (such as sodium). Such salts of the compounds of formula I and Ia are included within the scope of this invention.

Compounds of formula XII and the isothiouronium precursors (i.e. compounds of formula I wherein $D^1$ is —SH or —$SC(NH)NH_2$) are also within the scope of this invention.

Some of the compounds of formula Ia are known. Novel compounds of formula Ia are included in this invention.

This invention also provides pharmaceutical compositions comprising a compound of formula Ia or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included.

Sterile liquid form compositions include sterile solutions, suspensions, emulsions, syrups, and elixirs.

The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g. 25 mg to 250 mg, according to the particular need and activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound.

The following Examples illustrate the invention and methods for preparing compounds of the invention.

EXAMPLE 1

N-Butyl-4-chlorobenzenemethanamine

A solution of N-butyl-4-chlorobenzamide (2.26 g; 0.011 mol) in dry THF (25 ml) was added slowly to an ice-cooled solution of 1.0M $B_2H_6$—THF complex (45 ml; 0.045 mol) under a nitrogen blanket. When addition was complete, the mixture was stirred and heated to reflux for 3 hours, cooled and decomposed by dropwise addition of 1:1 conc aq HCl-water (10 ml). The mixture was then evaporated on a rotary evaporator at 60° for ½ hour to decompose the boron-amine complexes. The residue was taken up in water, strongly basified with aq NaOH and extracted with $CH_2Cl_2$ (3×25 ml). The combined extracts were washed with water, dried (MgSO$_4$), filtered and evaporated to give n-butyl-4-chlorobenzenemethanamine (1.79 g) as an oil. The oil was converted to the hydrochloride salt of the title compound (1.98 g) by crystallising from ethanolic HCl and ethyl acetate, mp 250°–252° after melting and resolidifying at 203°–207°.

Analysis $C_{11}H_{16}ClN.HCl$ requires: C, 56.4; H, 7.3; N, 6.0. Found: C, 56.4; H, 7.4; N, 6.2%.

EXAMPLE 2

N-(1-Methylbutyl)-4-chlorobenzenemethanamine

In a manner analogous to Example 1 a solution of N-(1-methylbutyl)-4-chlorobenzamide (2.26 g; 0.01 mol) in dry THF (25 ml) was reacted with an ice-cooled solution of 1.0M.$B_2H_6$—THF complex (45 ml; 0.045 mol) under a nitrogen blanket to give the title compound as an oil.

The oil was converted to the hydrochloride salt (1.58 g) by crystallising from ethanolic HCl and ethyl acetate, mp 170°–171°.

Analysis $C_{12}H_{18}ClN.HCl$ requires: C, 58.1; H, 7.7; N, 5.6. Found: C, 58.2; H, 8.0; N, 6.0%.

EXAMPLE 3

N-Butyl-N-methyl-4-chlorobenzenemethanamine

In a manner analogous to Example 1 a solution of N-butyl-N-methyl-4-chlorobenzamide (4.49 g; 0.02 mol) in dry THF (50 ml) was reacted with an ice-cooled solution of 1.0M diborane-THF complex (90 ml); 0.09 mol) to give the title compound which was converted to the hydrochloride salt and crystallised from ethyl acetate (1.51 g; 65.7%), mp 136°–138°.

Analysis $C_{12}H_{18}ClN.HCl$ requires: C, 58.1; H, 7.7; N, 5.6. Found: C, 58.3; H, 7.7; N, 5.8%.

EXAMPLE 4

N-Butyl-N-methylbenzenemethanamine

Benzyl chloride (1.15 ml; 0.01 mol) was added dropwise to a vigorously stirred, ice-cold solution of N-methylbutylamine (10 ml; large excess) in ethanol (30 ml). The clear solution was then kept at room temperature for 2 days, evaporated to dryness, the residue taken up in water and dil HCl and washed with ether (2×25 ml) and the combined extracts dried (MgSO$_4$). Filtration and evaporation gave a yellow oil (1.68 g) which was converted to the HCl salt with ethereal HCl, the solvents evaporated and the residue crystallised twice from ethyl acetate to give the title compound as the hydrochloride, quarterhydrate (0.6 g), mp 115°–118°.

Analysis $C_{12}H_{19}N.HCl.\frac{1}{4}H_2O$ requires: C, 66.0; H, 9.5; N, 6.4. Found: C, 65.6; H. 9.5; N, 6.4%.

EXAMPLE 5

N,N-Bis-(4-chlorobenzyl)butylamine

A solution of N-n-butyl-N-(4-chlorobenzyl)-4-chlorobenzamide (2.9 g; 8.6 mmol) in dry tetrahydrofuran (25 ml) was added to a 1.0M solution of diborane in tetrahydrofuran (43 ml; 43 mmol). The mixture was stirred for ½ hour at 0°, then stirred and heated to reflux for 3 hours. After cooling, the mixture was decomposed by cautious addition of 1:1 aq-conc HCl (20 ml) at 0°. The solvents were evaporated and the white residue, which was extensively complexed with boron, was stirred and heated to reflux with 1:1 aq-conc HCl (70 ml) for 7¼ hours. After cooling, a heavy oil separated. The oil was extracted into dichloromethane (3×25 ml) and the combined extracts were washed with brine and dried (MgSO$_4$). Filtration and evaporation gave a pale-yellow syrup (1.41 g).

The syrup was converted to the free base with aq NaOH and extracted into dichloromethane. After drying (MgSO$_4$) and evaporation, chromatography on silica eluted with toluene afforded the product (1 g), an oil, as the first product eluted. This was converted to the HCl salt with ethereal HCl. The solvent was evaporated and the residue was crystallised from ethyl acetate-ether to give, in two crops, the title compound as the hydrochloride salt (0.93 g), mp 174°–178°.

Analysis

C$_{18}$H$_{21}$Cl$_2$.HCl requires: C, 60.3; H, 6.2; N, 3.9. Found: C, 60.3; H, 6.2; N, 4.2%.

EXAMPLES 6–10

By analogous procedures to those herein described the following compounds of formula Ib were prepared:

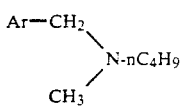

where Ar has the following meaning:

| Example No | Ar | Melting Point |
|---|---|---|
| 6 | 4-hydroxyphenyl | 135–137° C. (hemioxalate hemihydrate) |
| 7 | 2-methoxy-phenyl | 121–123° C. (oxalate, hydrate) |
| 8 | 4-chloro-2-methoxyphenyl | 142–144° C. (oxalate) |
| 9 | 2,6-dimethyl-phenyl | 83–84.5° C. (maleate) |
| 10 | 4-amino-5-chloro-2-methoxy phenyl | 167–174° C. (dec) (dihydrochloride) |

EXAMPLE 11

N-Butyldibenzylamine

A solution of N,N-dibenzylbutyramide (2.67 g) in tetrahydrofuran (10 ml) was added dropwise over 10 minutes to a stirred suspension of lithium aluminium hydride (1.52 g) in tetrahydrofuran (40 ml) at 90° C. The mixture was refluxed for 14 hours and was quenched by the dropwise addition of water (1.61 ml), 2N aqueous sodium hydroxide (3 ml) and water (3 ml). The white mixture was stirred at room temperature for 1 hour and was filtered. The residue was washed with tetrahydrofuran (2×10 ml) and the combined filtrate and washings were concentrated in vacuo. Diisopropyl ether (50 ml) was added and the mixture was washed with saturated aqueous sodium chloride (1×10 ml), dried (Na$_2$SO$_4$) and concentrated in vacuo to give an orange oil (2.43 g). The product was chromatographed on silica with eluent diisopropyl ether and distilled bulb to bulb to give the title compound as the free base (1.82 g, 72%, bp 160° C./0.5 mm Hg. Ether (20 ml) and ethereal hydrogen chloride (5 ml) were added. The mixture was concentrated in vacuo and the product crystallised slowly in ether at room temperature to give the hydrochloride hemihydrate salt (1.79 g), mp 131°–133° C.

Analysis

C$_{18}$H$_{23}$N.HCl.0.5H$_2$O requires: C, 72.35; H, 8.1; N, 4.7%. Found: C, 72.6; H, 8.3; N, 4.6.

EXAMPLE 12

N,N-Dibenzyl-diaminobutane

A solution of 4-(N,N-dibenzylamino)butyramide HCl (0.01 mol) in dry THF (50 ml) was added dropwise to a solution of LiAlH$_4$ (3.25 g; 0.0855 mol) in dry THF (50 ml). The mixture was stirred and heated to reflux for 2 hours, cooled, then decomposed by dropwise addition of water (3 ml), 15% aq NaOH (3 ml) and water (9 ml). After filtration, the filtrate was dried (MgSO$_4$), filtered and evaporated to give an oil (2.95 g). The oil was dissolved in hot ethanol (5 ml) and treated to give an oil (2.95 g). The oil was dissolved in hot ethanol (5 ml) and treated with oxalic acid (1.0 g; 1 equiv). The solution was filtered hot, diluted with ethyl acetate, cooled and crystals collected by filtration. Recrystallisation twice from ethanol-ether gave the ¾ ethanedioate salt (1.34 g) as very pale cream crystals, mp 156°–167° (dec, softens above 150°).

Analysis

C$_{18}$H$_{24}$N$_2$.¾(COOH)$_2$ requires: C, 69.7; H, 7.7; N, 8.3. Found: C, 69.3; H, 7.7; N, 8.1%.

EXAMPLE 13

N,N-Bis-(4-chlorobenzyl)-1,4-diaminobutane

A solution of 4-[N,N-bis-(4-chlorobenzyl)amino]-butyronitrile (2.2 g; 0.0066 mol) in dry THF (25 ml) was added dropwise to an ice-cooled solution of 1.0M BH$_3$—THF (40 ml; 0.04 mol) under a nitrogen blanket. The mixture was then stirred and heated to reflux for 7 hours. After cooling, the mixture was decomposed by dropwise addition of 1:1 conc HCl-water (30 ml). The solvents were evaporated in vacuo and the solid residue was boiled with water (50 ml) and conc H$_2$SO$_4$ (20 ml) for 4 hours. After cooling, the mixture was rendered basic with aq NaOH, extracted with CH$_2$Cl$_2$ (3×30 ml) and the combined extracts washed with water and dried (MgSO$_4$). Filtration and evaporation gave a gum (1.59 g) which was chromatographed on silica eluted with neat ethyl acetate. Further elution with a solution of 2% Et$_3$N-20% EtOH-78% ethylacetate afforded a gum (1.52 g) which was dissolved in hot ethanol and treated with one equivalent of oxalic acid, diluted with ether and cooled. Crystallisation occurred slowly to give a solid, which was recrystallised from ethanol to give the title compound as the ¾ oxalate salt (0.76 g), mp 158°–166° (decomp).

Analysis

C$_{18}$H$_{22}$Cl$_2$N$_2$.¾(COOH)$_2$ requires: C, 57.9; H, 5.85; N, 6.9. Found: C, 57.9; H, 6.0; N, 7.0%.

EXAMPLE 14

N-(3-Chloropropyl)dibenzylamine

The title compound as the hydrochloride salt was prepared by halogenating N-(3-hydroxypropyl)dibenzylamine using thionyl chloride, mp 118°–121° (dec).

Analysis

C$_{17}$H$_{20}$ClN.HCl requires: C, 65.8; H, 6.8; N, 4.5. Found: C, 65.7; H, 6.9; N, 4.7%.

EXAMPLE 15

S-[4-(N,N-Dibenzyl)aminobutyl]isothiourea

A mixture of N-(3-chloropropyl)dibenzylamine (1.98 g; 7.2 mmol) prepared according to Example 14, and thiourea (0.55 g, 7.2 mmol) in ethanol (25ml) was stirred and heated to reflux for 17 hours. The solution was then cooled and the solvent evaporated to give a residual oil. The oil was triturated with ether, and crystals formed overnight. The crystals were collected by filtration and recrystallized from isopropanol-ethyl acetate to give crystals of the title compound as the hydrochloride, quarterhydrate (1.09 g), mp 139°–141° C.

Analysis $C_{18} H_{23} N_3 S$ HCl, $\frac{1}{4}$ $H_2O$ requires: C,61.0; H,7.0; N,11.9 Found: C, 60.8; H,6.9; N,11.9%

EXAMPLE 16

3-[N,N-Bis-benzyl]aminopropanesulphonic acid a) S-[(N,N-dibenzyl)aminobutyl]isothiourea, hydrochloride (prepared according to Example 15) was hydrolysed in aqueous ethanolic sodium hydroxide. The solvents were evaporated and the residue taken up in water and extracted 3 times with methylene dichloride. The extracts were dried (MgSO$_4$), filtered and evaporated to give N-(3- mercaptopropyl)dibenzylamine.

b) A solution of the mercapto compound prepared in step a) above (4.18 g, 0.015mol) in acetic acid (50 ml) and water (50 ml) was cooled to 0° (ice-bath) then stirred vigorously as a solution of bromine (7.84 g; 0.049mol) in acetic acid (50 ml) was added dropwise. The evolved gas was entrained in a water trap. When addition of the bromine solution was complete, the mixture was stirred at room temperature for one hour. The solvents were then evaporated in vacuo, and the residue was stripped twice with water. The residual gum was boiled with water for 4.75 hours by which time the mixture was dissolved completely. The solution was cooled and evaporated to dryness to give 3-[N,N-bis-benzyl]aminopropanesulphonic acid as an oil.

This was purified by C-18 reverse-phase hplc, eluted with 2.5M ammonium acetate in 25-75 acetonitrile/water buffered at pH3.5. The product was found to be organically pure but contained one molar equivalent of ammonium acetate.

EXAMPLE 17

2-[N-Butyl-N-methyl]naphthalenemethanamine a) 2-Naphthoyl chloride (3.81 g 0.020 moles) dissolved in dichloromethane (10 ml) was added dropwise to an ice cold solution of N-methylbutylamine (1.74 g, 0.020 moles) and diisopropylethylamine (4.5 ml, 0.025 moles) in dichloromethane (40 ml). The mixture was stirred at room temperature for 18 hours and evaporated in vacuo. The residue was taken up into dichloromethane (50 ml), washed with 2M HCl (2×25 ml), dried (MgSO$_4$) then evaporated in vacuo to give N-butyl-N-methyl-naphthalene-2-carboxamide (4.6 g, 0.019 moles) as a yellow oil.

b) A 10M solution of borane/methyl sulphide in tetrahydrofuran (5 ml, 0.05 moles) was added dropwise to a solution of the product of step (a) dissolved in anhydrous tetrahydrofuran (75 ml). The mixture was heated at reflux for 18 hours, cooled to 20° C., then a 5M solution of sulphuric acid (20 ml) was added dropwise over one hour. The mixture was stirred for one hour, then dimethyl sulphide and tetrahydrofuran were distilled out of the reaction mixture at 80° C. Further 5M sulphonic acid (10 ml) was added and the mixture refluxed for 1½ hours then stirred at room temperature for 16 hours. The mixture was basified with 2M sodium bicarbonate, extracted with dichloromethane (2×50 ml), dried (MgSO$_4$) and evaporated in vacuo to give the title compound (3.95 g, 0.017 moles) as a yellow oil. Tosylic acid (3.23 g, 0.017 moles) was dissolved in isopropanol (20 ml), then added to the above product. Evaporation in vacuo and crystallisation from ethyl acetate/toluene gave the toluene-4-sulphonic acid salt (4.15 g, 52%) as a white solid mp 124°–127° C.

Analysis $C_{16}H_{21}N.C_7H_8SO_3$ requires: C,69.2; H,7.32; N,3.51 Found: C,69.2; H,7.18; N,3.47%

EXAMPLE 18

1-[N-Butyl-N-methyl]naphthalenemethanamine a) A solution of 1-naphthoyl chloride (3.81 g, 0.020 moles) dissolved in dichloromethane (10 ml), was added dropwise to an ice-cold solution of N-methylbutylamine (1.74 g 0.020 moles) and diisopropylethylamine (4.5 ml, ca 0.025 moles) dissolved in dichloromethane (50 ml). The mixture was stirred at room temperature for 18 hours, then evaporated in vacuo, taken up into dichloromethane (50 ml), washed with dilute hydrochloric acid (2×25 ml), dried (MgSO$_4$) then evaporated in vacuo to give 1-(n-butyl-N-methyl)bnaphthalenecarboxamide (4.46 g, 0.018 moles).

b) To the product of step (a) dissolved in tetrahydrofuran (25 ml) was added a 10M solution of borane/methyl sulphide in tetrahydrofuran (5 ml, 0.05 moles). The mixture was then heated at reflux for 18 hours, then was cooled to room temperature. 5M Sulphuric acid (20 ml) was added dropwise, the mixture was stirred for one hour and then the solvents and methylsulphide were distilled off. Sulphuric acid (10M, 10 ml) was added and the mixture refluxed for 1½ hours. After cooling and evaporation in vacuo, the residue was taken up into aqueous sodium bicarbonate (50 ml), extracted with dichloromethane (2×100 ml), dried (MgSO$_4$) and then evaporated in vacuo to give the title compound (4.2 g, 0.017 moles) as an oil (4.2 g, 0.017 moles). To this was added toluene-4-sulphonic acid (3.23 g, 0.017 moles), and the mixture was heated in ethanol/ethyl acetate to give on cooling crystals of the toluene-4-sulphonic acid salt of the title compound (3.97 g) mp 126°–130° C.

Analysis $C_{16}H_{21}N.C_7H_8SO_3$ requires: C,69.1; H, 7.32; N,3.51 Found: C,68.8; H,7.40; N,3.40%.

EXAMPLE 19

3-(1,2-Diphenylethylamino)-Propanesulphonic Acid Sodium Salt

A solution of 12.2 g of 3-hydroxy-1-propane sulphonic acid γ-sultone, 19.7 g of 1,2-diphenyl-ethylamine and 150 ml of methanol was left standing at room temperature for 72 hours. The precipitated solid was separated and suspended in boiling methanol. After cooling to room temperature the solid was separated and suspended in boiling methanol. After cooling to room temperature the solid was separated and dried in vacuo. The resulting solid was stirred with 1 liter of methanol and 2.792 g of sodium hydroxide until a clear solution formed. Removal of the solvent in vacuo afforded 22 grams of the title compound as the quarter hydrate, mp 285°–290° C.

Analysis

Calcd for $C_{17}H_{21}NO_3SNa.\frac{1}{4}H_2O$; C,58.85; H,6.25;N,4.04;S,9.24 Found: C,58.46;H,5.81;N,4.01;S,9.36.

EXAMPLE 20

3-[(Diphenylmethyl)amino]-1-Propanesulphonic Acid Sodium Salt

A solution of 18.3 g of aminodiphenyl methane, 12.2 g of 3-hydroxy-1-propane sulphonic acid γ-sultone and 200 ml of methanol were left standing at room temperature for 72 hours. The gummy precipitate was separated and dissolved in a mixture of isopropanol and ethanol. A crystalline precipitate formed on standing.

The solid was separated and dissolved in 800 ml of methanol. The solution was evaporated to the point of crystallization, cooled and filtered to obtain 12 grams of a solid.

The solid was suspended in 300 ml of methanol and titrated with 2N sodium hydroxide solution. The solution was evaporated in vacuo to obtain 12.6 g of the title compound as the two-thirds hydrate, mp. 150°–4° C. dec.

Analysis:

Calcd. for $C_{16}H_{18}NO_3SNa.2/3H_2O$: C,56.64;H,5.73; N,4.13 Found: C,56.90;H,5.68;N,4.13.

EXAMPLE 21

3-(2,2-Diphenylethylamino)-1-Propanesulphonic Acid Sodium Salt

A solution of 12.2 g of 3-hydroxy-1-propane sulphonic acid γ-sultone, 19.7 g of 2,2-diphenylethylamine and 270 ml of methanol was left standing at room temperature for 48 hours. The precipitate solid was separated by filtration and washed with methanol. The solid was dried in vacuo to obtain 15.3 g of 3-(2,2-diphenylethylamino)-1-propanesulphonic acid, mp 283°–5° C.(dec).

Analysis:

Calc for $C_{17}H_{21}NO_3S$; C,63.92; H,6.63; N, 4.39; S,10.04 Found: C,63.98; H,6.87; N,4.49; S,9.96.

The sodium salt was prepared by dissolving 11.36 g of the acid and 1.424 g of sodium hydroxide in 500 ml of methanol. Removal of the solvent in vacuo afforded 8.6 g of the title compound, mp 283°–5° C.

Analysis:

Calcd for $C_{17}H_{20}NO_3SNa$: C,59.81;H,5.91;N,4.10; S,9.39 Found: C,59.62; H,5.98; N,4.01; S,9.01.

We claim:

1. A method of treating depression or cerebral insufficiency disorders or dementias in a mammal so afflicted, which comprises administering to said mammal an amount effective to alleviate depression or cerebral insufficiency or dementias of a compound having the formula

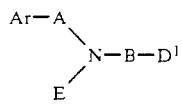

or a pharmaceutically acceptable salt thereof, wherein

E represents hydrogen, lower alkyl or a group Ar$^1$—A$^1$—;

Ar and Ar$^1$ are, independently, mono- or bi-cyclic aryl groups of 6 to 10 carbon atoms which are optionally substituted by one to three substituents independently selected from lower alkyl, lower alkoxy, halogen, haloloweralkyl, haloloweralkoxy, cyano, amino, mono- or di-loweralkyl amino and nitro;

A and A$^1$ are, independently, —(CH$_2$)$_m$—, where m is 1 or 2, optionally substituted by a lower alkyl group or an Ar$^2$ group, wherein Ar$^2$ is the same or different as Ar defined above, or by one of each such group;

B is an alkylene group of 3 or 4 carbon atoms, which may be substituted by lower alkyl; and D$^1$ represents halogen, —CH$_3$, —CR$^1$R$^2$NH$_2$, —SO$_3$H or —SO$_2$NR$^6$R$^7$, where R$^1$ and R$^2$ are independently hydrogen or lower alkyl and R$^6$ and R$^7$ are each hydrogen, lower alkyl or aralkyl of 7 to 12 carbon atoms or R$^6$ and R$^7$ together with the nitrogen atom to which they are attached represent a 5 or 6 membered ring.

2. A method as claimed in claim 1 in which Ar an Ar$^1$ when present are selected from optionally substituted phenyl or naphthyl.

3. A method as claimed in claim 1 in which the optional substituents for Ar and Ar$^1$ when present are selected from lower alkyl, lower alkoxy, halogen, haloloweralkyl, haloloweralkoxy, cyano, amino and nitro.

4. A method as claimed in claim 1 wherein A and A$^1$ independently represent —CHR$^3$—, where R$^3$ is hydrogen, lower alkyl or optionally substituted aryl as defined for Ar.

5. A method as claimed in claim 1 wherein B is —CH$_2$CH$_2$CH$_2$— or such a group substituted by methyl.

6. A method as claimed in claim 1 wherein D$^1$ is —CH$_3$, —SO$_3$H or —SO$_2$NH$_2$.

7. A method as claimed in claim 1 in which the compound of formula Ia is N-butyl-4-chlorobenzenemethanamine or a salt thereof.

8. A method as claimed in claim 1 in which the compound of formula Ia is N-(1-methylbutyl)-4-chlorobenzenemethanamine or a salt thereof.

9. A method as claimed in claim 1 in which the compound of formula Ia is N-butyl-N-methyl-4-chlorobenzenemethanamine or a salt thereof.

10. A method as claimed in claim 1 in which the compound of formula Ia is N-butyl-N-methylbenzenemethanamine or a salt thereof.

11. A method as claimed in claim 1 in which the compound of formula Ia is N,N-bis-(4-chlorobenzyl)-butylamine or a salt thereof.

12. A method as claimed in claim 1 in which the compound of formula Ia is N-butyldibenzylamine or a salt thereof.

13. A method as claimed in claim 1 in which the compound of formula Ia is N,N-dibenzyl-1,4-diaminobutane or a salt thereof.

14. A method as claimed in claim 1 in which the compound of formula Ia is N-(3-chloropropyl)dibenzylamine or a salt thereof.

15. A method as claimed in claim 1 in which the compound of formula Ia is 3-[N,N-benzyl]aminopropanesulphonic acid or a salt thereof.

16. A pharmaceutical composition comprising an amount effective to alleviate depression or cerebral insufficiency or dementias a compound having the formula

or a pharmaceutically acceptable salt thereof, wherein
E represents hydrogen, lower alkyl or a group $Ar^1$-$A^1$;

Ar and $Ar^1$ are, independently, mono- or bi-cyclic aryl groups of 6 to 10 carbon atoms which are optionally substituted by one to three substituents independently selected from lower alkyl, lower alkoxy, halogen, haloloweralkyl, haloloweralkoxy, cyano, amino, mono- or diloweralkyl amino and nitro;

A and $A^1$ are, independently, —$(CH_2)_m$—, where m is 1 or 2, optionally substituted by a lower alkyl group or an $Ar^2$ group, wherein $Ar^2$ is the same or different as Ar defined above, or by one of each such group;

B is an alkylene group of 3 or 4 carbon atoms, which may be substituted by lower alkyl; and $D^1$ represents halogen, —$CH_3$—, —$CR^1R^2NH_2$, —$SO_3H$ or —$SO_2NR^6R^7$, where $R^1$ and $R^2$ are independently hydrogen or lower alkyl and $R^6$ and $R^7$ are each hydrogen, lower alkyl or aralkyl of 7 to 12 carbon atoms or $R^6$ and $R^7$ together with the nitrogen atom to which they are attached represent a 5 or 6 membered ring, with the proviso that (i) when $D^1$ is —$CH_2NH_2$, then B is other than —$(CH_2)_4$—, providing that when B is —$(CH_2)_3$—, then Ar—A is other than unsubstituted benzyl;

(ii) when $D^1$ is chlorine, Ar—A is other than benzyl; and (iii) when $NR^6R^7$ represents a 5- or 6-membered ring, Ar represents optionally substituted phenyl and A represents ethylene optionally substituted by lower alkyl, then E is other than lower alkyl, and a pharmaceutically acceptable carrier.

17. A composition as claimed in claim 16 in which Ar and $Ar^1$ when present are selected from optionally substituted phenyl or naphthyl.

18. A composition as claimed in claim 16 in which the optional substituents for Ar and $Ar^1$ when present are selected from lower alkyl, lower alkoxy, halogen, haloloweralkyl, haloloweralkoxy, cyano, amino and nitro.

19. A composition as claimed in claim 16 wherein A and $A^1$ independently represent —$CHR_3$— where $R^3$ is hydrogen, lower alkyl or optionally substituted aryl as defined for Ar.

20. A composition as claimed in claim 16 wherein B is —$CH_2CH_2CH_2$— or such a group substituted by methyl.

21. A composition as claimed in claim 16 wherein $D^1$ is —$CH_3$, —$SO_3H$ or —$SO_2NH_2$.

22. A composition as claimed in claim 16 in which the compound of formula Ia is N-butyl-4-chlorobenzenemethanamine or a salt thereof.

23. A composition as claimed in claim 16 in which the compound of formula Ia is N-(1-methylbutyl)-4-chlorobenzenemethanamine or a salt thereof.

24. A composition as claimed in claim 16 in which the compound of formula Ia is N-butyl-N-methyl-4-chlorobenzenemethanamine or a salt thereof.

25. A composition as claimed in claim 16 in which the compound of formula Ia is N-butyl-N-methylbenzenemethanamine or a salt thereof.

26. A composition as claimed in claim 16 in which the compound of formula Ia is N,N-bis(4-chlorobenzyl)-butylamine or a salt thereof.

27. A composition as claimed in claim 16 in which the compound of formula Ia is N-butyldibenzylamine or a salt thereof.

28. A composition as claimed in claim 16 in which the compound of formula Ia is N,N-dibenzyl-1,4-diaminobutane or a salt thereof.

29. A composition as claimed in claim 16 in which the compound of formula Ia is N-(3-chloropropyl)dibenzylamine or a salt thereof.

30. A composition as claimed in claim 16 in which the compound of formula Ia is 3-[N,N-benzyl]aminopropanesulphonic acid or a salt thereof.

* * * * *